United States Patent [19]

Tai

[11] Patent Number: 4,760,172

[45] Date of Patent: Jul. 26, 1988

[54] PROCESS FOR THE PREPARATION OF OPTICALLY ACTIVE 2-(4-METHOXYPHENOXY) PROPIONIC ACID

[75] Inventor: Jimmy J. Tai, Midland, Mich.

[73] Assignee: The Dow Chemical Company, Midland, Mich.

[21] Appl. No.: 945,426

[22] Filed: Dec. 22, 1986

[51] Int. Cl.$^4$ .............................................. C07B 57/00
[52] U.S. Cl. ...................................... 562/401; 560/61; 562/471
[58] Field of Search .................... 562/401, 471; 560/61

[56] References Cited

U.S. PATENT DOCUMENTS

| | | | |
|---|---|---|---|
| 4,035,416 | 7/1977 | Brust | 562/471 |
| 4,173,709 | 11/1979 | Metivier et al. | 562/401 |
| 4,309,547 | 1/1982 | Koch et al. | 560/61 X |
| 4,532,346 | 7/1985 | Rehn et al. | 562/471 |

FOREIGN PATENT DOCUMENTS 0192849 9/1986 European Pat. Off. .
2486071 1/1982 France .

*Primary Examiner*—Werren B. Lone
*Assistant Examiner*—Vera C. Clarke
*Attorney, Agent, or Firm*—S. Preston Jones; Ronald G. Brookens

[57] ABSTRACT

A process for the preparation of optically active 2-(4-methoxyphenoxy)propionic acid of at least 75 percent enantiomeric excess of the desired optical isomer comprised of contacting 2-chloropropionic acid or a lower alkyl ester or an alkali metal salt thereof, having an optical purity greater than 85 percent of the opposite configuration, with from 3 to 10 molar equivalents of 4-methoxyphenol in an aqueous base.

6 Claims, No Drawings

PROCESS FOR THE PREPARATION OF OPTICALLY ACTIVE 2-(4-METHOXYPHENOXY) PROPIONIC ACID

BACKGROUND OF THE INVENTION

Optical isomers are often known to have enhanced biological activity over the corresponding racemates. For example, European Patent Application No. 159,864 discloses the enhanced activity of S(−)-2-(4-methoxyphenoxy)propionic acid as a taste modifier and sweetness inhibitor. Similarly, European Patent Application Nos. 2,800 and 3,890 teach the utility of R(+)-2-(4-hydroxyphenoxy)propionic acid as an intermediate for the production of R(+)-(pyridyloxyphenoxy)propionic acid derivatives which display greater herbicidal activity than the racemates. In turn, R(+)-2-(4-methoxyphenoxy)propionic acid is a desirable intermediate for the preparation of the optically active (hydroxyphenoxy)propionic acid.

Various methods for obtaining high concentrations of optical isomers are known. In addition to the resolution of a racemic mixture into its optically active components which, for example, depends on the conversion to diastereomers and subsequent physical separation, individual enantiomers can be obtained by direct synthesis employing an appropriate optically active starting material. For example, optically active 2-substituted propionic acids are conveniently prepared by the reaction of either an optically active 2-halopropionic acid or an optically active alkyl or aryl sulfonate of lactic acid with an appropriate nucleophile. Such nucleophilic displacement reactions generally occur with inversion of configuration of the asymmetric carbon atom of the starting material Therefore, to prepare the R-enantiomer of the 2-substituted propionic acid, the S-enantiomer of the 2-halopropionic acid or sulfonate ester of lactic acid is employed as the starting material.

Theoretically, one can obtain essentially 100 percent of the desired enantiomer by this method. In practice, however, the optical purity of the final product is largely determined by (a) the optical purity of the starting material, (b) the nature of the leaving group and (c) the specific conditions employed. Typically, one obtains products containing a ratio of from 70 to 90 percent of the desired enantiomer and, correspondingly, 10 to 30 percent of the other optical isomer. Such products are then said to possess an optical purity of 40 to 80 percent, i.e., from 40 to 80 percent of the mixture is the desired enantiomer and from 20 to 60 percent is a racemic mixture.

The importance of the nature of the leaving group in the starting propionic acid is illustrated in the article of G. Sakata et al. in J. Pesticide Sci., 10, 69-73 (1985). Products of the following optical purities were obtained with different leaving groups under comparable conditions: tosylate (∼80 percent): mesylate (∼45 percent): bromide (∼45 percent): and chloride (∼10 percent). Thus, although optically active 2-chloropropionic acid derivatives may be the most preferable starting material from the viewpoint of cost and availability, they are the least advantageous with respect to optical purity of the product.

Similarly, the importance of the reaction conditions is well known. For example, as shown in U.S. Pat. No. 4,532,328, the optical purity of the final product can be substantially enhanced by employing a 5 to 20 fold molar excess of the optically active starting material. Although enhanced optical yields are achieved, large amounts of relatively expensive optically active reagents such as S-methyl 2-chloropropionate must be recovered and recycled. Furthermore, this reagent may be susceptible to racemization under the reaction and recovery conditions thus precluding its direct recycle in the process.

SUMMARY OF THE INVENTION

The present invention provides a process for making optically active 2-(4-methoxyphenoxy)propionic acid of enhanced optical purity of at least 75 percent which comprises contacting one equivalent of an optically active 2-chloropropionic acid, a $C_1$–$C_4$ lower alkyl ester or an alkali metal salt thereof with a stoichiometric excess of 4-methoxyphenol in the presence of an aqueous base.

It is well understood that such reactions occur with inversion of the configuration of the asymmetric center of the chloropropionic acid starting material. For example, the S-form of the 2-chloropropionic acid starting material is required to produce the R-form of the product.

The enhanced optical purity of the product is related to the amount of methoxyphenol used in excess of one molar equivalent. In order to achieve optical purities exceeding 75 percent of a particular enantiomer, it is necessary to employ at least 3 equivalents of methoxyphenol and a 2-chloropropionic acid derivative containing at least an 85 percent excess of the appropriate enantiomer (92.5:7.5).

The upper range of the amount of methoxyphenol to be used in excess is generally determined by an evaluation of the degree of optical purity of the product which is desired and the incremental cost of recovering and recycling the excess methoxyphenol. Typically, amounts of methoxyphenol in the range of 3 to 10 molar equivalents per mole of 2-chloropropionic acid, ester or salt are desired. Preferably, amounts in the range of 3 to 5 molar equivalents are employed.

The excess of methoxyphenol is advantageously recovered during the reaction workup. For example, by adjusting the pH of the alkaline reaction mixture with acid so that the phenate is converted to the phenol while the desired carboxylic acid remains as the water-soluble salt form, the methoxyphenol can be recovered by extraction with an organic solvent.

With this approach, the optically active starting material is essentially completely consumed. Thus, racemization associated with recovery and recycle of the optically active reagent is avoided. Thus the present invention avoids the shortcomings of the prior art in the utilization of 2-chloropropionic acid and its derivatives for preparing optically active 2-substituted propionic acids.

Furthermore, the process of this invention is conducted in an aqueous medium, thus obviating the need for polar aprotic organic solvents or azeotropic drying procedures typically employed for such reactions.

The reaction is generally carried out at atmospheric pressure. However, operation at reduced or elevated pressures is equally operable.

Similarly, the reaction can be conducted from ambient temperature to the reflux temperature of the mixture, but the range of about 60° to about 90° C. is preferred.

When using the lower alkyl esters of 2-chloropropionic acid as the starting material, the alkali metal salt of the product is obtained under the reaction conditions by saponification. Similarly, the free acid itself is neutralized to the alkali metal salt. Therefore, sufficient base must be added to allow for neutralization of the acid or saponification of the ester in addition to that necessary to stoichiometrically convert the methoxyphenol to the corresponding phenate. Generally, the one molar equivalent of base necessary to achieve saponification or neutralization of the propionate in addition to the one molar equivalent required to ionize all of the methoxyphenol present or a 5 to 30 percent excess of the total amount is desirable.

Any base sufficiently strong to substantially ionize the 4-methoxyphenol without interfering with the reaction or subsequent workup is contemplated. Such bases include the alkali metal (Li+, Na+, K+) carbonates and hydroxides with sodium and potassium hydroxide being the most preferred.

After completion of the reaction, the mixture is alkaline. By adjusting the pH of the mixture to substantially convert the excess phenate to the phenol while maintaining the product in the form of the alkali metal salt, the excess methoxyphenol can be recovered in substantially pure form by extraction with an immiscible organic solvent. Such solvents include chlorinated hydrocarbons e.g., methylene chloride or perchloroethylene, aromatics e.g., chlorobenzene and ketones e.g., methyl isobutyl ketone. The 4-methoxyphenol, suitable for recycle in the process, can be recovered by evaporation of the solvent.

After removal of the excess methoxyphenol, the pH of the remaining aqueous reaction mixture is typically adjusted with a strong mineral acid, e.g. HCl or $H_2SO_4$ to convert the product to the free acid form. The 2-(4-methoxyphenoxy)propionic acid of high optical purity can be obtained by extraction with an immiscible organic solvent, preferably the same solvent used to recover the methoxyphenol, followed by evaporation of that solvent.

The R-enantiomer of 2-(4-methoxyphenoxy)propionic acid is capable of giving rise to the R-enantiomer of 2-(4-hydroxyphenoxy)propionic acid which in turn is a useful intermediate for the preparation of the R-enantiomers of (pyridyloxyphenoxy)propionic acids of formula I

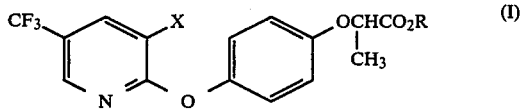

wherein X is hydrogen, fluorine, chlorine, bromine or iodine and wherein R is a hydrogen, alkyl, or alkoxy substituted alkyl group of from 1 to 8 carbon atoms. These materials are herbicides useful for the post-emergent control of graminaceous weeds in broad-leaf crops as indicated hereinabove.

In order to prepare R-2-(4-hydroxyphenoxy)propionic acid, the R-2-(4-methoxyphenoxy)propionic acid prepared as described herein can be demethylated according to standard procedures, see for example "Reagents for Organic Synthesis" by L. F. Fieser and M. Fieser, volume 1, p 452 (1967). Treatment with 48 percent hydrobromic acid cleaves the methyl group to provide methyl bromide and 2-(4-hydroxyphenoxy)propionic acid of retained configuration and comparable optical purity. Since the R-2-(4-hydroxyphenoxy)propionic acid is in the free acid form, it can be preferably esterified by conventional esterification procedures to produce an alkyl or alkoxyalkyl ester of from 1 to 8 carbon atoms.

The herbicides of formula I can be prepared according to the procedures disclosed in European Patent Application Nos. 2800 and 3890. Thus, the R-2-(4-hydroxyphenoxy)propionic acid or ester so obtained can be further reacted with a compound of formula II

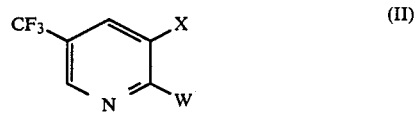

wherein X is hydrogen, fluorine, chlorine, bromine or iodine and wherein W is a leaving group e.g. fluorine, chlorine, bromine or iodine. When the compounds of formula I are in the free acid form, they are preferably esterified employing conventional ester formation procedures to produce agriculturally acceptable esters which include, for example, the following: methyl, ethyl, propyl, butyl, octyl, ethoxyethyl, butoxyethyl and methoxypropyl.

DETAILED DESCRIPTION OF THE INVENTION

The following examples illustrate the invention.

EXAMPLE 1

Preparation of R-2-(4-methoxyphenoxy)propionic acid

To 148.8 grams (g) (1.2 mole) of 4-methoxyphenol in a 500 ml flask equipped with a mechanical stirrer, condenser, addition funnel and heating mantle was added 256 g (1.6 mole) of 25 percent NaOH. The solution was then heated to 65° C. and 36.6 g (0.3 mole)of S-methyl 2-chloropropionate (approximately 86 percent optical purity) was added to the reaction mixture. The mixture was heated to 85° C. and stirred for 30 minutes. After cooling to room temperature, the pH of the solution was adjusted to between 5.0–6.0 with concentrated HCl. Methyl iso-butyl ketone was used to extract the unreacted 4-methoxyphenol which was subsequently recovered by evaporation of the solvent. The pH of the aqueous phase was further adjusted to about 1.0 with concentrated HCl. Methyl iso-butyl ketone was again used to extract the product. After removing the solvent, 46.6 g (79 percent yield) of R-2(4-methoxyphenoxy)propionic acid was obtained. The material had a melting range of 54°–59° C. after drying. The nuclear magnetic resonance spectrum was consistent with the structure. The enantiomer ratio of R to S was found to be 88 to 12 (76 percent optical purity) by capillary gas chromatography on a DB-1 column after derivatization with S(+)-2-aminopropanol.

EXAMPLE 2

Preparation of S-2-(4-methoxyphenoxy)propionic acid

Following the procedure of Example 1, but substituting 99 percent optically pure R-methyl 2-chloropropionate for the previously used S-enantiomer, S-2-(4-methoxyphenoxy)propionic acid was isolated in approximately 80 percent yield. The product had an R to S enantiomer ratio of 6 to 94 (88 percent optical purity).

EXAMPLE 3

Preparation of S-2-(4-hydroxyphenoxy)propionic acid

S-2-(4-methoxyphenoxy)propionic acid (39.2 g) was melted at 90° C. and 85.6 g of concentrated HBr was slowly added. The reaction mixture exothermed to 110° C. The mixture was stirred at 105° C. for four hours while methyl bromide was vented through a scrubber. The mixture was cooled to ambient temperature and the product was extracted from the aqueous mixture with methyl iso-butyl ketone. Evaporation of the solvent gave 34.5 g (95 percent yield) of S-2-(4-hydroxyphenoxy)propionic acid of the same optical purity (88 percent) as that of the starting material.

EXAMPLE 4

Preparation of R-2-(4-hydroxyphenoxy)propionic acid

Under conditions similar to those of Example 3 but substituting R-2-(4-methoxyphenoxy)propionic acid for the corresponding S-enantiomer, R-2-(4-hydroxyphenoxy)propionic acid is obtained in good yield and of comparable optical purity to the starting material.

EXAMPLE 5

Preparation of R-methyl 2-(4-hydroxyphenoxy)propionate

To 867.4 g (4.77 moles) of R-2-(4-hydroxyphenoxy)propionic acid (88 percent optical purity) in a 5 l flask equipped with a thermometer, mechanical stirrer and reflux condenser was added 2625 ml of methanol, 50 g of Dowex ® MSC-1H+ion exchange resin and 820 ml of 2,2-dimethoxypropane. The mixture was heated at reflux (65° C.) for 10 hours at which time less than 1 percent free acid remained. The mixture was cooled and the resin catalyst was removed by filtration. After evaporation of the volatile components, 915 g (98 percent yield) of R-methyl 2-(4-hydroxyphenoxy)propionate of 88 percent optical purity was obtained.

Various modifications may be made in the present invention without departing from the spirit or scope thereof, and it is understood that I limit myself only as defined in the appended claims.

What is claimed is:

1. A process for the preparation of optically active 2-(4-methoxyphenoxy)propionic acid of at least a 75 percent enantiomeric excess of the desired optical isomer which comprises contacting 2-chloropropionic acid, a $C_1$–$C_4$ lower alkyl ester or an alkali metal salt thereof, having an optical purity greater than 85 percent of the opposite configuration, with from 3 to 10 molar equivalents of 4-methoxyphenol in an aqueous base.

2. The process of claim 1 wherein the 2-chloropropionic acid derivative is of the S-configuration and the final product is R-2-(4-methoxyphenoxy)propionic acid.

3. The process of claim 1 wherein the base is sodium or potassium hydroxide.

4. The process of claim 1 wherein 4 to 5 molar equivalents of 4-methoxyphenol are employed.

5. A process according to claim 1 wherein the optically active product is demethylated to produce 2-(4-hydroxyphenoxy)propionic acid of retained configuration and comparable optical purity.

6. A process according to claim 5 wherein the free acid is subsequently esterified to produce an alkyl or alkoxyalkyl ester of from 1 to 8 carbon atoms.

* * * * *